United States Patent [19]

Spinner et al.

[11] 4,014,748
[45] Mar. 29, 1977

[54] ANAEROBIC CULTURE COLLECTING AND TRANSPORTING APPARATUS

[75] Inventors: Ernest Elliott Spinner, Grandview, Mo.; Myron Norton Slotsky, Overland Park, Kans.

[73] Assignee: Marion Laboratories, Inc., Kansas City, Mo.

[22] Filed: Dec. 22, 1975

[21] Appl. No.: 643,260

[52] U.S. Cl. .............................. 195/127; 195/139; 195/142; 128/2 W
[51] Int. Cl.² ......................................... C12K 1/00
[58] Field of Search ............... 195/103.5, 127, 142, 195/109, 139; 128/2 W

[56] References Cited
UNITED STATES PATENTS

| | | | |
|---|---|---|---|
| 3,246,959 | 4/1966 | Brewer | 195/109 X |
| 3,775,256 | 11/1973 | Risinger | 195/108 |
| 3,913,564 | 10/1975 | Freshley | 128/2 W |
| 3,939,044 | 2/1976 | Wilkins et al. | 195/127 X |

Primary Examiner—Lionel M. Shapiro
Attorney, Agent, or Firm—Merriam, Marshall, Shapiro & Klose

[57] ABSTRACT

A culture collecting and transporting apparatus comprising a closable container having a collected culture receiving depot therein, means in the container for supplying a culture medium to a culture placed on the depot, and chemical means in the container selectively activated after a culture is placed on the depot, said chemical means when activated supplying gaseous carbon dioxide, and a reducing agent system effective for reducing oxygen, at least in the container space surrounding the collected culture. The reducing agent system may comprise a reducing gas and a catalyst for inducing reaction of the oxygen with the reducing gas. The reducing gas may be hydrogen.

26 Claims, 9 Drawing Figures

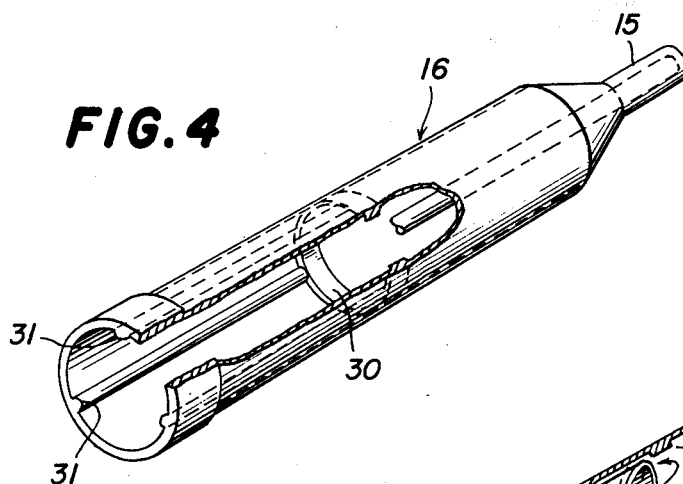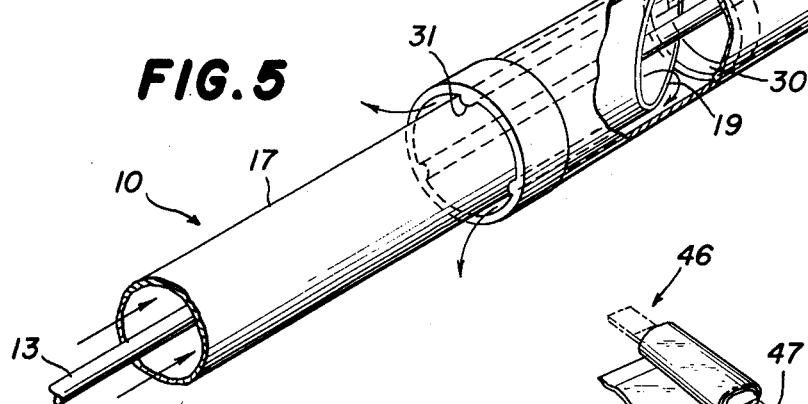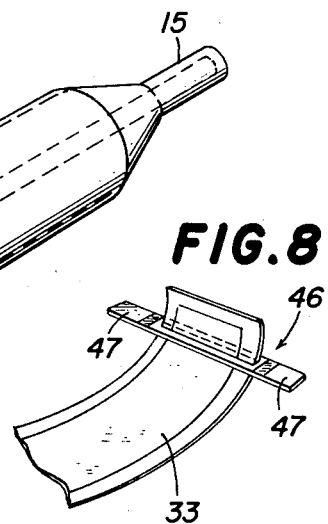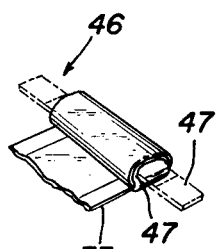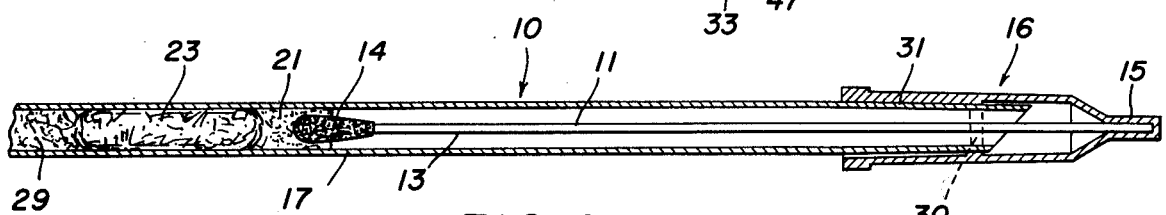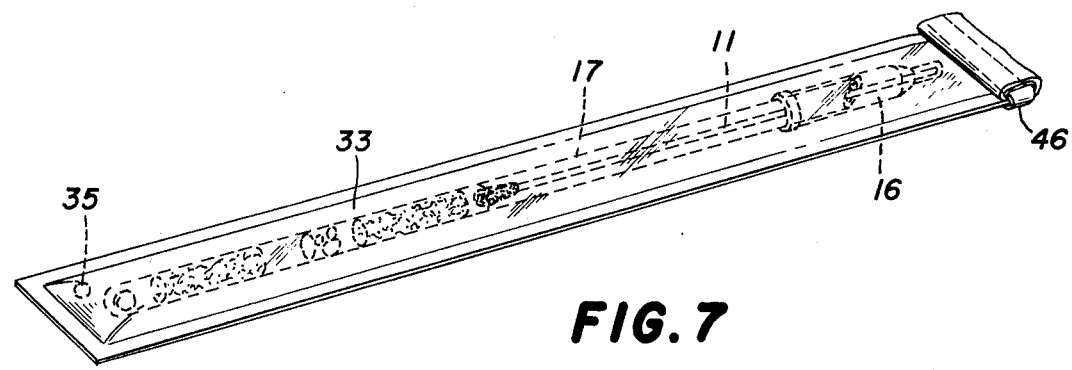

ANAEROBIC CULTURE COLLECTING AND TRANSPORTING APPARATUS

This invention relates to apparatus for collecting and transporting a bacterial culture in a viable state so that the culture can be subsequently tested in a laboratory. More particularly, this invention is concerned with an apparatus for collecting and transporting cultures of the type which remain viable only when in the presence of a particular gaseous environment or atmosphere.

Many diseases of man and lower animals are bacterial in origin. The treatment of many bacterial diseases requires that the infecting organism be identified. A drug known to be effective against the infecting organism can then be prescribed.

The identification of an infecting organism is generally by means of a culture obtained from the ill patient or animal. A conventional swab is often used for this purpose. After the culture is obtained on the swab it must then be handled carefully under conditions which prevent it from being contaminated by other organisms. The culture is then transported to a laboratory for determination of the identity of the infecting organism. Such laboratories require highly trained microbiologists and elaborate, expensive equipment. Suitable testing laboratories, accordingly, are not always readily available. It therefore becomes necessary for the patient or animal to visit the laboratory where the culture can be obtained and put immediately into the test procedures or for the culture to be taken at a location remote from the laboratory and then transported to the laboratory for testing.

While the collecting of a culture generally presents no difficulties, the storage and/or transportation of the culture to a testing laboratory under conditions which guarantee the culture will be viable and free of contamination upon arrival presents serious problems. Although contamination from other organisms can generally be avoided by suitable means, the maintenance of a viable culture often requires, in addition to a suitable nutrient medium, the storage and transportation of the culture in a particular gaseous environment which promotes its viability.

Since bacteria of the anaerobic type are known to require an oxygen-deficient or oxygen-free gaseous environment, it is obvious that the transportation of an anaerobic bacteria culture should be effected in an environment having no or little oxygen. Organisms which are obligate anaerobes, such as the bacilli of tetanus, gas-gangrene, botulinus and bacteroides, require the absence of oxygen for proper growth. Furthermore, there are other organisms which require special atmospheres for proper growth. Thus, the gonococcus, meningococcus and brucella require a substantially higher concentration of carbon dioxide than that of the atmosphere for proper growth. Although this is generally known by bacteriologists, it is disclosed in Brewer U.S. Pat. No. 3,246,959.

The Brewer U.S. Pat. No. 3,246,959 discloses a gas-producing device for generating an atmosphere conducive for maintaining and increasing the viability of organisms which require a special non-toxic atmosphere. The patent shows the generation of hydrogen, carbon dioxide and acetylene for the purpose of supplying a non-toxic atmosphere to a culture in a container. A platinized wire gauze in the container is heated by electricity for the purpose of completely reacting oxygen in the container. The patent does not say what the oxygen reacts with or what else is to be present in the container at that time.

Aronoff U.S. Pat. No. 3,773,035 and Patterson U.S. Pat. No. 3,750,646 each disclose culture collecting and transporting apparatus. The apparatus is used by collecting a culture on a swabbing tip and placing it in contact with a medium for sustaining the culture. The system of each patent is intended to maintain a carbon dioxide enriched atmosphere around the collected culture to promote its growth.

Avery et al. U.S. Pat. No. 3,450,129 also discloses a culture collecting and transporting unit. The unit constitutes an elongated plastic tube in which a swab used for the culture collecting is placed. A nutrient medium for the organism is supplied by rupturing an ampoule containing the liquid medium in the plastic tube. The unit does not contain a provision for controlling the atmosphere in the plastic tube.

Although the prior art discloses culture collecting and transporting apparatus which provides a controlled gaseous atmosphere around a collected culture, there is a need for more convenient and efficient apparatus for this purpose. This is particularly so when it is desired to control more than one gaseous component in the space surrounding a collected culture.

According to one aspect of the invention there is provided a culture collecting and transporting apparatus comprising a closable container having a collected culture receiving depot therein, means in the container for supplying a culture nutrient or transport medium to a culture placed at the depot, and chemical means in the container selectively activated after the culture is placed at the depot, said chemical means when activated supplying gaseous carbon dioxide, and a reducing agent system effective for reducing oxygen, at least in the container space surrounding the collected culture. The invention, however, is also concerned with novel apparatus which supplies only a reducing gas such as hydrogen, without also supplying carbon dioxide, as will be seen from the subsequent disclosure.

The culture receiving depot is either self-contained with respect to a suitable nutrient or transport medium for the culture or the depot can be supplied with a nutrient or transport medium from a supply ampoule, containing a nutrient or transport medium, in the container.

The apparatus generally includes, as part of the combination thereof, a suitable swab comprising an elongated stem with a swabbing tip at one end. The swab may be enclosed in the container and be removed to collect a culture on the swabbing tip. The swab may then be replaced in the container with the swabbing tip positioned to be supplied, or placed in contact, with a nutrient or transport medium. The nutrient or transport medium provides the food for sustaining life of the culture and its growth during storage and transportation.

Included as part of the chemical means in the apparatus are ingredients which when combined produce gaseous carbon dioxide. Any combination of materials which safely and conveniently produce carbon dioxide can be employed for this purpose.

The chemical means also includes an ingredient or combination of ingredients which supplies a reducing agent system for reducing the oxygen present in the container. The reducing agent system generally includes a solid material which when contacted with a liquid from an adjacent ampoule or receptacle will liberate a gas having a reducing action.

The chemical means in a most useful form constitutes a solid material which supplies carbon dioxide when contacted with a liquid, and a solid material which when contacted with the same liquid supplies a reducing gas which reacts with oxygen in the presence of an activating agent. Furthermore, the liquid is advisably made available from an ampoule or similar vial positioned adjacent or close to the solid gas generating materials.

The container is generally provided with a dehydrating agent, preferably in solid form, to remove water and water vapor therefrom which may enter the container during sterilization, such as by ethylene oxide, in the manufacturing process or to remove water vapor which may penetrate the container in one way or another.

As a further means of controlling the atmosphere inside of the container and in the space surrounding the collected culture, the container may be placed inside of a receptacle which completely surrounds the container. This receptacle can be a flexible bag-like element. The receptacle aids in maintaining the container free of contamination during storage and transportation. In addition, the atmosphere in the container may be further controlled by preventing oxygen from entering the container from the receptacle by removing oxygen from the receptacle. This is achieved by providing a catalyst in the receptacle which will induce reaction between oxygen therein and a reducing gas, such as hydrogen, which is vented from the container interior. In this way the gaseous environment in the container is maintained devoid of or substantially lower in oxygen content than is otherwise achieved.

The invention will be described further in conjunction with the attached drawings, in which:

FIG. 4 is a fragmentary perspective view of the container closure or cap;

FIG. 5 is a fragmentary perspective view showing the closure as temporarily positioned on the container after a culture has been collected and the swab has been reinserted in the container;

FIG. 6 is a fragmentary longitudinal cross-sectional view similar to FIG. 3 but showing the swab in its final position in the container after the collection of a culture;

FIG. 7 is a perspective view showing the apparatus replaced in the receptacle or bag and closed by a metal clip and ready for temporary storage and transport to a laboratory;

FIG. 8 is a fragmentary perspective view showing the open end of the receptacle being closed by a metal clip; and FIG. 9 is a fragmentary perspective view of the end of the receptacle shown in FIG. 8 after being rolled on itself by means of the metal clip.

So far as is practical, the same elements or parts which appear in the different views of the drawings will be identified by the same numbers.

Figure 3:
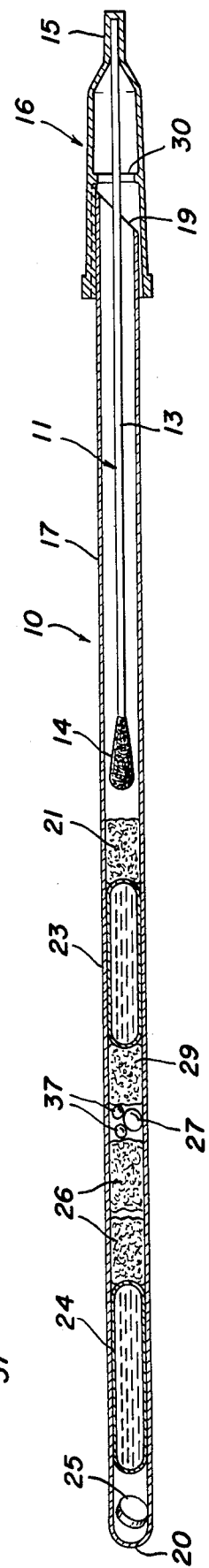
FIG. 3 is a cross-sectional view taken longitudinally through the container showing the swab as positioned in the container prior to use of the apparatus.
Figure 2:
FIG. 2 is a perspective view of the apparatus of FIG. 1 with the outer wrapper removed and with the container partially removed from the intermediate receptacle or bag, and with the swab removed from the container.
Figure 1:
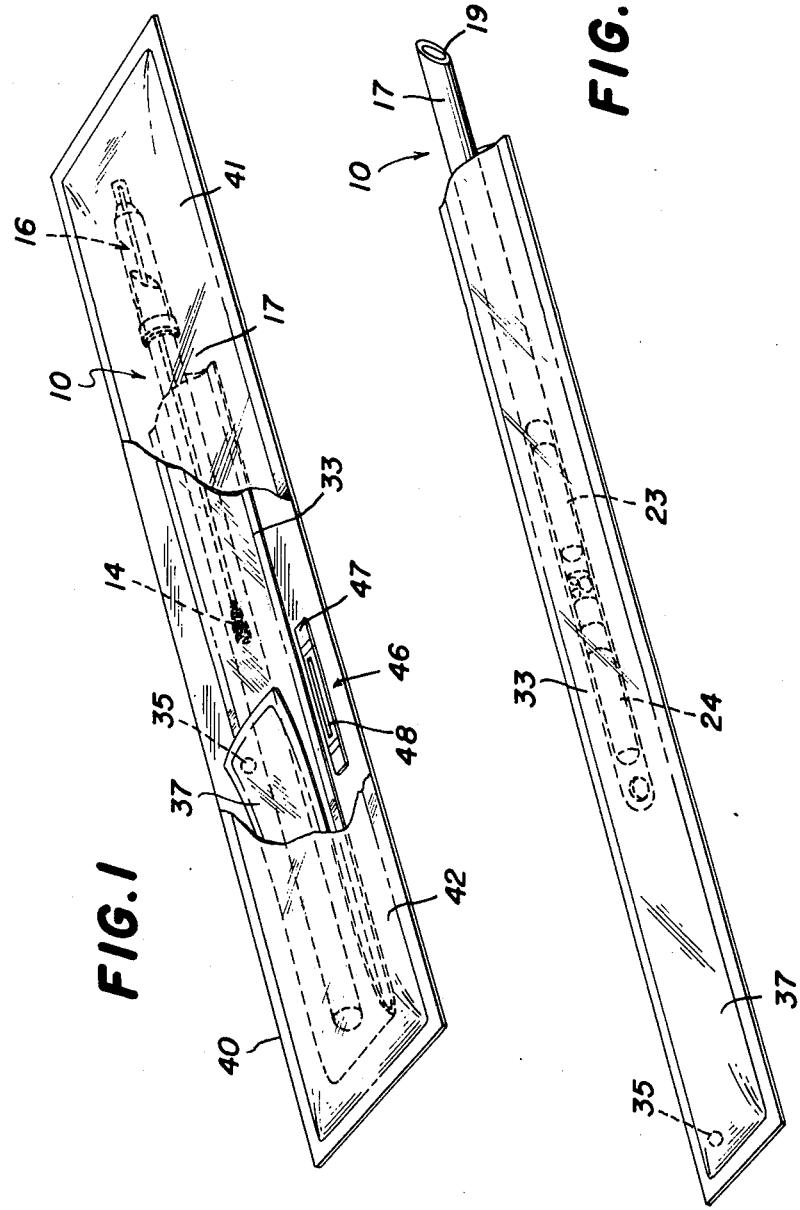
FIG. 1 is perspective view of a completely packaged culture collecting and transporting apparatus embodying all of the main aspects of the invention.

The completely packaged unit shown in FIGS. 1 to 3 has an outer wrapper 40, an inner or intermediate receptacle or bag 33 positioned within the outer wrapper 40, and a culture collecting and transporting container 10 positioned inside of the receptacle 33.

The outer wrapper 40 has a back sheet 41, which may be one made of a white sheet material such as Tyvek, and a top sheet 42 advisably made of a gas-permeable clear film or sheet material, which is bonded to the edges of the bottom sheet 41. Mylar is representative of commercially available materials suitable for sheet 42.

The receptacle 33 is shown in the drawings in the form of a bag, made of clear sheet or film material low in gas permeability, which is elongated and open at one end. The culture collecting and transporting container 10 is only partially inserted into the receptacle 33 to facilitate removal of the closure or cap 16 therefrom together with the associated swab 11. The closed end 37 of the receptacle 33 is folded back upon itself as shown in FIG. 1 to facilitate positioning it inside of outer wrapper 40. The receptacle 33 is made longer than the container 10 so that it can receive the entire length of the container 10 and be subsequently closed at its open end.

With reference to FIG. 3 of the drawings, the container 10 comprises an elongated plastic tube 17 having a beveled open end 19 covered by removable closure 16, and an opposite closed end 20. The tube 17 may be made of a flexible but self-supporting plastic such as transparent polyethylene, polypropylene or a polypropylene copolymer available as Avisun 6011. The closure or cap 16 telescopes over the open end 19 of tube 17. Sealing ring 30 is positioned inside closure 16 about midway of its length. Longitudinal ribs 31 are also positioned inside of the closure 16 and extend from the ring 30 to the open end of the closure to facilitate sliding the closure over the tube end.

The closure 16 has a reduced diameter tubular extension 15 at its top having a hole therein into which fits one end of the stem 13 of swab 11. The closure 16 thus also serves as a handle for the swab 11. A swabbing tip 14 is provided at the working end of swab 11. The swabbing tip 14 can be made of any suitable fibrous material such as cotton or polyester fibers. The closure 16 can be made of any suitable material but advisably is made of a somewhat flexible polymeric material such as polyethylene. As shown in FIG. 3 the swabbing tip 14 is maintained out of contact with gas permeable polyester plug 21 which may function alone, but advisably in combination with the swabbing tip, as a culture-receiving depot therein. The plug 21 is telescoped snugly within tube 17.

Ampoule 23, contining a suitable liquid mutrient or transport medium for the culture collected by swabbing tip 14, is positioned in tube 17 adjacent plug 21. The ampoule 23 can be made of glass or some other frangible or rupturable material which will permit release of the liquid medium from the ampoule by the application of finger pressure thereto from the outside of tube 17. Ampoule 23 can be filled with a medium such as a modified Cary-Blair transport media having the following composition:

| | | |
|---|---|---|
| Calcium chloride | 0.1 | g. |
| Disodium phosphate | 0.1 | g. |
| Sodium chloride | 5.0 | g. |
| Sodium bisulfite | 0.1 | g. |
| Agar | 0.8 | g. |
| Sodium thioglycolate | 2.2 | g. |
| L-Cysteine hydrochloride hydrate | 0.723 | g. |
| Distilled water | To one liter | |

The ampoule 23 can be 1–7/16 inch long and can contain 0.67 ml. of the modified Cary-Blair transport media.

A second ampoule 24 is located in tube 17 near the closed end 20. The ampoule 24 contains a suitable liquid. The ampoule, for example, can be 1–13/16 inches long and be filled with 1 ml. of 0.65 N hydrochloric acid.

Tablet or pellet 25 is positioned in tube 17 between the tube end 20 and the adjacent end of ampoule 24. The composition of tablet 25 may be as follows:

| | | |
|---|---|---|
| Potassium borohydride | 13 | mg. |
| Zinc | 13 | mg. |
| Sodium chloride | 15 | mg. |
| Sodium bicarbonate | 52.5 | mg. |
| Lactose DT | 47 | mg. |
| Microporous cellulose--Avicel PH102 | 57.5 | mg. |
| Tabletting lubricant--Calcium stearate | 2.0 | mg. |

A filter formed of two liquid absorbent plugs 26 are telescoped tightly into tube 17 adjacent the end of ampoule 24. These plugs are formed of a liquid absorbent material, such as polyester fibers, but the plugs are gas permeable. The plugs 26 thus permit gas to pass toward the open end of tube 17 from the gas generating area where tablet 25 is located. The plugs 26, furthermore, keep the liquid, when released from ampoule 24, away from the space around the swabbing tip 14 and plug 21.

A polyester fiber plug 29 is positioned adjacent the inner end of ampoule 23 containing the liquid nutrient or transport medium. A small space is provided between plug 29 and the end of plug 26. The space between the liquid absorbent plugs 26 and 29 is provided to receive solid catalyst 27. Although not a part of the broad invention, it is advisable to also include the desiccant, or moisture sequestering, solid pellets 37 in the same space as the catalyst 27. The pellets 37 can be molecular sieves or some other solid material such as calcium chloride or magnesium sulfate which has an effective dehydrating or moisture-sequestering action. The pellets 37 are intended to function as a desiccant and to protect the tube 17 contents from moisture during sterilization, such as with ethylene oxide, and to also maintain the tubular contents dry during storage and shipment of the culture collecting unit prior to its use and activation.

The entire packaged unit, as shown in FIG. 1, may be sterilized after packaging by subjecting the sealed outer wrapper 40 and the entire unit to a sterilizing gas, such as ethylene oxide. The sterilizing gas passes through the gas permeable film or sheet 41 and thus sterilizes the internal contents, including the container 10 and the receptacle 33. The moisture sequestering pellets 37 prevent the sterilizing gas from affecting the gas generating tablet 25 during sterilization.

The packaged unit, as shown in FIG. 1, is used by separating the outer wrapper 40 from the internal receptacle or bag 33. The outer wrapper 40 is removed by peeling away top film 41 from the bottom paper sheet 42. The inner receptacle 33 as freed from the outer wrapper 40 has the tube 17 projecting at least partially therein such as shown in FIG. 2. The closure 16 is then pulled longitudinally off of the end of tube 17. The swab 11 is removed simultaneously with the closure 16 which functions as a handle for the swab as is also shown in FIG. 2. A culture is then collected on the swabbing tip 14 and the swab is then immediately telescoped back into tube 17 through the tube open end 19. The closure 16 is telescoped onto the tube 17 sufficiently far to place the swabbing tip 14 in contact with the plug 21. When the closure is so positioned, integral ring 30 on the inside of the closure 16 presses against the outer surface of the open end portion of tube 17 as is shown in FIG. 6. The tube 17 is then positioned vertically with the closure 16 at the bottom. Tube 17 is then squeezed adjoining the ampoule 23 so as to break the ampoule and thereby release the liquid medium which flows to plug 21 and saturates it and the swabbing tip 14. In this way the collected culture is supplied with nutrients needed to maintain it viable during storage and transportation. After a few seconds the tube 17 containing the closure 16 is pushed fully into the receptacle 33. The open end of the receptacle 33 is then positioned in slot 48 (FIG. 8) of metal clip 46 which is stored in outer wrapper 40 as shown in FIG. 1. The clip is then used to roll the end of the receptacle 33 upon itself about three times to thereby effectively close the end. The ears 47 of clip 46 are then folded back 180° as shown in FIGS. 7 and 9 to prevent the end of the receptacle from unrolling. The resulting package is then rotated into vertical position with the closure 16 in top position. The ampoule 24 is then broken by squeezing tube 17. The acid in the ampoule 24 is thereby released and flows into contact with tablet 25. Reaction of the acid with the potassium borohydride causes hydrogen to be generated within the tube while reaction of the acid with the sodium bicarbonate results in the generation of carbon dioxide. Both of these gases flow through the entire length of tube 17 since all of the plugs therein are gas permeable. Plugs 26 absorb the acid and prevent it from flowing elsewhere in the tube. The liquid acid also combines with ingredients of tablet 25 to form a slush which further serves to hold the liquid acid in place. The hydrogen intermixes with the oxygen in tube 17 and by means of the catalyst 27 these two gases react to form water, thereby scavenging oxygen from the internal space of tube 17.

The receptacle 33 is made from a transparent material of low gas permeability, such as a laminate identified as No. CL5040 (Clear Lam Products). The receptacle 33 protects the container 10 from the external ambient atmosphere. Furthermore, as the carbon dioxide and hydrogen are generated in tube 17 a considerable amount of it escapes past closure 16 in the space between the closure and the outer surface of the end of tube 17. The gases which so escape enter receptacle 33, containing catalyst pellet 35 located therein. The immediate effect is for the gases to cause the receptacle to balloon or expand outwardly to its nonelastic limit. The ballooning effect is evidence that the gases have generated as expected. However, immediately upon entry of hydrogen into receptacle 33 the catalyst pellet 35 induces reaction of the hydrogen with the oxygen to form water. A 5% palladium-on-alumina pellet is suitable for this purpose. Other active catalysts may, of course, be used for this purpose. The described catalytic removal of oxygen from receptacle 33 does not significantly effect the ballooning. However, by about forty-eight hours or so after the unit is activated the carbon dioxide may have permeated the receptacle wall causing a vacuum to develop in the receptacle. The atmospheric pressure then will press or collapse the receptacle walls, when flexible, together and against the tube. This condition may result even without oxygen entering the receptacle because the gas permeability of the receptacle wall material may permit flow of carbon dioxide but not oxygen.

The described culture collecting and transporting apparatus is particularly suitable for use with cultures which require either a carbon dioxide enriched atmosphere or at least a substantially oxygen-free atmosphere, or an atmosphere enriched in carbon dioxide but at least substantially oxygen-free, to survive in a viable form for a substantial time between collection and testing. The apparatus thus can be used to transport an organism which requires only an increased carbon dioxide concentration in the atmosphere and which remains viable whether oxygen is present or not. Furthermore, the apparatus can be used to transport an organism which requires an atmosphere which is oxygen-free, or substantially oxygen-free, and which remains viable whether or not there is an increase in the carbon dioxide concentration in the atmosphere. The apparatus, however, is particularly useful when it is desired that the atmosphere surrounding a culture sample be enriched in carbon dioxide but decreased at least substantially in oxygen content.

When the culture collecting and transporting container 10 is sealed in a receptacle 33 as described herein and oxygen is removed by means of the catalyst pellet 35, a culture can be maintained in a viable condition in tube 17 for up to 96 hours. The novel container 10, however, is useful without receptacle 33 but the anaerobic conditions therein are not maintained as long as when the receptacle 33 is also used. The anaerobic condition is not as readily maintained in tube 17 without receptacle 33 because it is not readily possible to mass produce closures 16 with sufficiently precise tolerances to establish a tight enough seal to prevent gas flow around the open end of tube 17 even when the closure 16 is in so-called sealing position. Without use of receptacle 33 a culture generally will not be maintained viable in tube 17 for much longer than 24 hours. This, however, is an adequately long period for transport of cultures in some highly developed urban areas. Accordingly, the container 10 without the receptacle 33 is considered to constitute a highly useful culture collecting and transporting apparatus.

The described apparatus may also be modified for storage and transportation of anaerobic organism cultures which do not require a carbon dioxide enriched atmosphere in container 10 by omitting the sodium bicarbonate from tablet 25.

It is also contemplated that the swab 11 may be omitted from the apparatus or packaged separately and apart from closure 16. A conventional swab separately available in a doctor's office or health center can be used to take the culture sample. The swab can then be put in container 10 and left there with the swab tip in contact with plug 21. Nutrient medium can then be supplied to the culture as previously described herein.

Furthermore, it is also considered feasible in some instances to discard the swab, after the plug 21 has been innoculated with the culture and impregnated with the nutrient medium, rather than to have it remain in container 10.

It is also within the scope of the invention to use an agar slant in tube 17 in place of the ampoule 23 and to deposit the collected culture on the agar slant.

The chemical means suitable for generating the gaseous carbon dioxide in the apparatus of this invention is not to be limited to the specific embodiment set forth herein. Other well known chemical means for gaseous carbon dioxide generation may be used. Broadly, any solid material which upon contact with a liquid releases carbon dioxide in adequate amount in a reasonably short time may be used. The least expensive method, of course, is to contact a carbonate or bicarbonate salt with a dilute acid which will not produce vapors having an adverse effect on the culture. Instead of putting a dilute acid in the ampoule it can be filled with water, and sodium bicarbonate and citric acid, or some suitable acid salt, can be put in pellet 25 to generate carbon dioxide. Other feasible systems will appear readily to skilled chemists.

Although the above example illustrates the production of hydrogen as the reducing gas by the use of specific chemicals, i.e. potassium borohydride, zinc, sodium chloride and dilute hydrochloric acid, other solid materials can be used in conjunction with other liquids to produce hydrogen or some other suitable gas which will react catalytically with oxygen to remove it from the space around the culture. Thus, water alone can be placed in ampoule 24 and the solid pellet 25 can be formulated to contain a material which reacts with water safely and reasonably quickly to produce hydrogen. Thus, sodium borohydride, lithium aluminum hydride, lithium hydride, calcium hydride, aluminum hydride and lithium borohydride can be used since they react with water or aqueous acid to form hydrogen. Such hydrides also react with other liquids such as alcohols to form hydrogen so that sometimes it may be desirable to replace the water with an alcohol, provided it does not adversely affect the culture. Hydrogen can, of course, be produced by the reaction of a metal such as iron, zinc, aluminum and magnesium with a suitable acid such as sulfuric acid and hydrochloric acid.

Instead of using hydrogen as the reducing gas to remove oxygen from the tube 17, it is feasible to form acetylene by the reaction of calcium carbide in pellet 25 and water or dilute acid in ampoule 24.

The foregoing detailed description has been given for clearness of understanding only, and no unnecessary limitations should be understood therefrom, as modifications will be obvious to those skilled in the art.

What is claimed is:

1. A culture collecting and transporting apparatus comprising:
    an elongated tube having an open end with a removable closure thereon and an opposite closed end;
    a swab having an absorbent swabbing tip located within said tube and having an elongated stem located adjacent the open end of the tube;
    a first frangible ampoule disposed within said tube adjacent said swabbing tip, said ampoule containing a liquid nutrient medium which, when released from said ampoule, moistens said swabbing tip;

a gas producing agent located within said tube between the tube closed end and the nutrient medium ampoule;

a second frangible ampoule located within said tube adjacent said gas producing agent, said second ampoule containing an activating liquid which, when released from said second ampoule, flows into reactive contact with said gas producing agent to cause hydrogen to be generated within said tube; and said tube being made of flexible material to enable the liquids in said ampoules to be released by squeezing the tube inwardly to rupture the ampoules; and a filter located between said ampoules, said filter being gas permeable and liquid impermeable.

2. A culture collecting and transporting apparatus as defined in claim 1 in which said gas producing agent and said activating liquid react to generate hydrogen and carbon dioxide in said tube.

3. A culture collecting and transporting apparatus as defined in claim 1 further including a catalyst within said tube for inducing said hydrogen to react with oxygen in said tube.

4. A culture collecting and transporting apparatus as defined in claim 1 further including a dehydrating agent in the tube.

5. A culture collecting and transporting apparatus as defined in claim 1 in which said gas producing agent is a solid material.

6. A culture collecting and transporting apparatus as defined in claim 1 further including a receptacle for receiving said tube, said receptacle being made of a flexible material which is gas impermeable.

7. A culture collecting and transporting apparatus as defined in claim 6 further including a catalyst located within said receptacle and outside of said tube for inducing a reducing gas generated within said tube to react with oxygen within the receptacle.

8. A culture collecting and transporting apparatus as defined in claim 6 further including an outer wrapper for receiving said receptacle, said outer wrapper being made of a flexible and gas permeable material.

9. A culture collecting and transporting apparatus comprising:

a closable container having a collected culture receiving depot therein, means in the container for supplying a culture medium to a culture placed on the depot, chemical means in the container selectively activated after a culture is placed on the depot, said chemical means when activated supplying gaseous carbon dioxide and hydrogen at least in the container space surrounding the collected culture, the chemical means including a deposit of solid material and an ampoule of a liquid which is reactable with the solid material to produce gaseous carbon dioxide and hydrogen, and a catalyst in the container for inducing reaction between oxygen and hydrogen.

10. A culture collecting and transporting apparatus according to claim 9 in which the chemical means includes a solid carbonate or bicarbonate salt reactable with the liquid to form carbon dioxide.

11. A culture collecting and transporting apparatus according to claim 9 in which the chemical means includes a solid metal hydride or a metal reactable with the liquid to form hydrogen.

12. A culture collecting and transporting apparatus according to claim 9 in which the container is located inside of a receptacle, and the receptacle also has a catalyst which catalyzes reaction of hydrogen with oxygen to remove oxygen therefrom, and the container has means for venting hydrogen therefrom to the receptacle.

13. A culture collecting and transporting apparatus according to claim 9 in which the container has a desiccant therein.

14. A culture collecting and transporting apparatus according to claim 9 in which the culture medium is a liquid in a frangible rupturable ampoule.

15. A culture collecting and transporting apparatus comprising:

a closable container having a collected culture receiving depot therein, in the container a frangible rupturable ampoule containing a liquid nutrient medium to be supplied to a culture placed on the depot, and chemical means in the container selectively activated after a culture is placed on the depot, said chemical means when activated supplying gaseous carbon dioxide, and a reducing agent system effective for reducing oxygen, at least in the container space surrounding the collected culture.

16. A culture collecting and transporting apparatus according to claim 15 in which the container has a desiccant therein.

17. A culture collecting and transporting apparatus according to claim 16 in which the reducing agent system comprises a reducing gas and a catayst for inducing reaction of the oxygen with the reducing gas.

18. A culture collecting and transporting apparatus according to claim 17 in which the reducing gas is hydrogen.

19. A culture collecting and transporting apparatus according to claim 18 in which the container is located inside of a receptacle, and the receptacle also has a catalyst which catalyzes the reaction of hydrogen with oxygen to remove oxygen therefrom, and the container has means for venting hydrogen therefrom to the receptacle.

20. A culture collecting and transporting apparatus comprising:

a closable container havng a swab positioned therein for removal and replacement after a culture is collected by the swab, a desiccant in the container, a culture medium in the container for supplying to a culture collected by the swab when the swab is replaced in the container, said culture medium being out of water vapor contact with the desiccant until the apparatus is used, and chemical means in the container selectively activated after the swab with the collected culture is replaced in the container, said chemical means when activated supplying gaseous carbon dioxide, and a reducing agent effective for reducing oxygen, at least in the container space surrounding the collected culture.

21. A culture collecting and transporting apparatus comprising:

a closable container having a collected culture receiving depot therein, a desiccant in the container, and chemical means in the container selectively activated after a culture is placed on the depot, said chemical means when activated supplying gaseous carbon dioxide, and a reducing agent system effective for reducing oxygen, at least in the container space surrounding the collected culture.

22. A culture collecting and transporting apparatus comprising:
a closable container having a swab positioned therein for removal and replacement after a culture is collected by the swab,
means in the container for supplying a culture medium to a culture deposited in the container,
chemical means in the container selectively activated after the swab with the collected culture is replaced in the container, said chemical means when activated supplying both gaseous carbon dioxide and hydrogen to at least the container space surrounding the collected culture,
means in the container for inducing reaction of oxygen therein with the hydrogen to produce water and thereby reduce or eliminate oxygen from the container at least in the space around and occupied by the collected culture,
the chemical means for supplying gaseous carbon dioxide and hydrogen including a deposit of solid material and an adjacent ampoule of aqueous acid, and which acid is reactable with the deposit of solid material to simultaneously produce gaseous carbon dioxide and hydrogen, and
the ampoule is openable to put the acid in contact with the solid material without other access of the acid to the container interior, and including barrier means in the container which bars flow of the freed acid into contact with the culture and the culture medium.

23. A culture collecting and transporting apparatus according to claim 22 in which the means for inducing reaction of the oxygen with the hydrogen is a catalyst.

24. A culture collecting and transporting apparatus according to claim 22 in which the container is located inside of a receptacle having a catalyst which catalyzes reaction of hydrogen with oxygen to remove oxygen therefrom.

25. A culture collecting and transporting apparatus according to claim 22 in which the container has a desiccant therein.

26. A culture collecting and transporting apparatus according to claim 22 in which the means for supplying a culture medium includes a frangible ampoule containing a liquid nutrient medium which, when released from said ampoule, moistens the swabbing tip.

* * * * *